(12) United States Patent
Weis et al.

(10) Patent No.: US 9,814,818 B2
(45) Date of Patent: Nov. 14, 2017

(54) DEVICE AND METHOD FOR DETECTING BLOOD OR BLOOD CONSTITUENTS IN THE LIQUID SYSTEM OF A DEVICE FOR EXTRACORPOREAL BLOOD TREATMENT

(75) Inventors: Manfred Weis, St. Wendel (DE); Martin Lauer, St. Wendel (GB); Stefan Kreber, Saarbruecken (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 838 days.

(21) Appl. No.: 13/498,643

(22) PCT Filed: Sep. 23, 2010

(86) PCT No.: PCT/EP2010/005826
§ 371 (c)(1),
(2), (4) Date: May 21, 2012

(87) PCT Pub. No.: WO2011/038858
PCT Pub. Date: Apr. 7, 2011

(65) Prior Publication Data
US 2012/0223016 A1    Sep. 6, 2012

(30) Foreign Application Priority Data

Sep. 29, 2009  (DE) .......................... 10 2009 043 284
Oct. 7, 2009  (DE) .......................... 10 2009 048 561

(51) Int. Cl.
*A61M 1/16* (2006.01)
(52) U.S. Cl.
CPC ............ *A61M 1/16* (2013.01); *A61M 1/1635* (2014.02)

(58) Field of Classification Search
None
See application file for complete search history.

(56) References Cited

U.S. PATENT DOCUMENTS 4,747,950 A    5/1988  Guinn
5,542,919 A *  8/1996  Simon et al. .................. 604/29
(Continued)

FOREIGN PATENT DOCUMENTS

DE    811 7448 U1    11/1981
DE    411 6177 C2    11/1992
(Continued)

OTHER PUBLICATIONS

International Search Report from PCT/EP2010/005826 dated Jan. 20, 2011.

*Primary Examiner* — Patrick Orme
(74) *Attorney, Agent, or Firm* — Kilyk & Bowersox, P.L.L.C.

(57) ABSTRACT

The present invention relates to an apparatus for dialysis treatment which has device(s) for balancing fresh and used dialysis fluid. The present invention also relates to a method of balancing fresh and used dialysis fluid. The apparatus and method according to the present invention for balancing fresh and used dialysis fluid are characterized in that the individual balancing chambers of the balancing system receive both fresh dialysis fluid and used dialysis fluid, the functions of the balancing chambers being alternately interchanged. In this way, exact balancing can be achieved even when the volumes of the individual chambers differ from one another. Over the period of the treatment as a whole, the differences between the volumes balance each other out due to the cyclic interchange of the chambers.

17 Claims, 8 Drawing Sheets

(56) References Cited

U.S. PATENT DOCUMENTS

| | | | |
|---|---|---|---|
| 2006/0200064 A1* | 9/2006 | Gross et al. | 604/5.01 |
| 2007/0038191 A1* | 2/2007 | Burbank et al. | 604/317 |
| 2007/0278155 A1* | 12/2007 | Lo et al. | 210/646 |

FOREIGN PATENT DOCUMENTS

| | | |
|---|---|---|
| DE | 198 30 928 C1 | 5/1999 |
| EP | 0 343 267 A1 | 11/1989 |
| EP | 0 687 474 A1 | 12/1995 |
| EP | 0 867 195 A1 | 9/1998 |
| EP | 1 393 761 A1 | 3/2004 |

\* cited by examiner

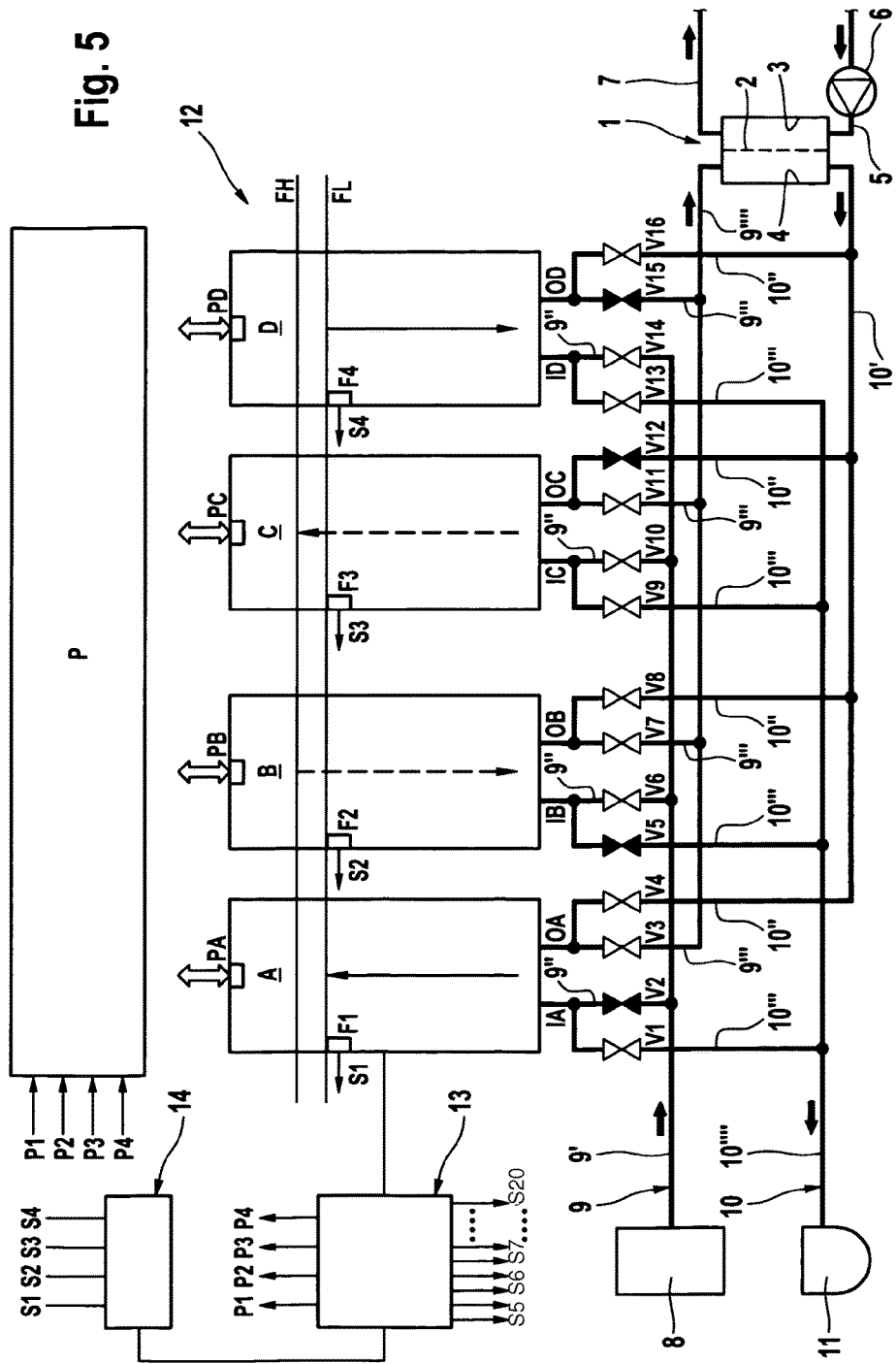

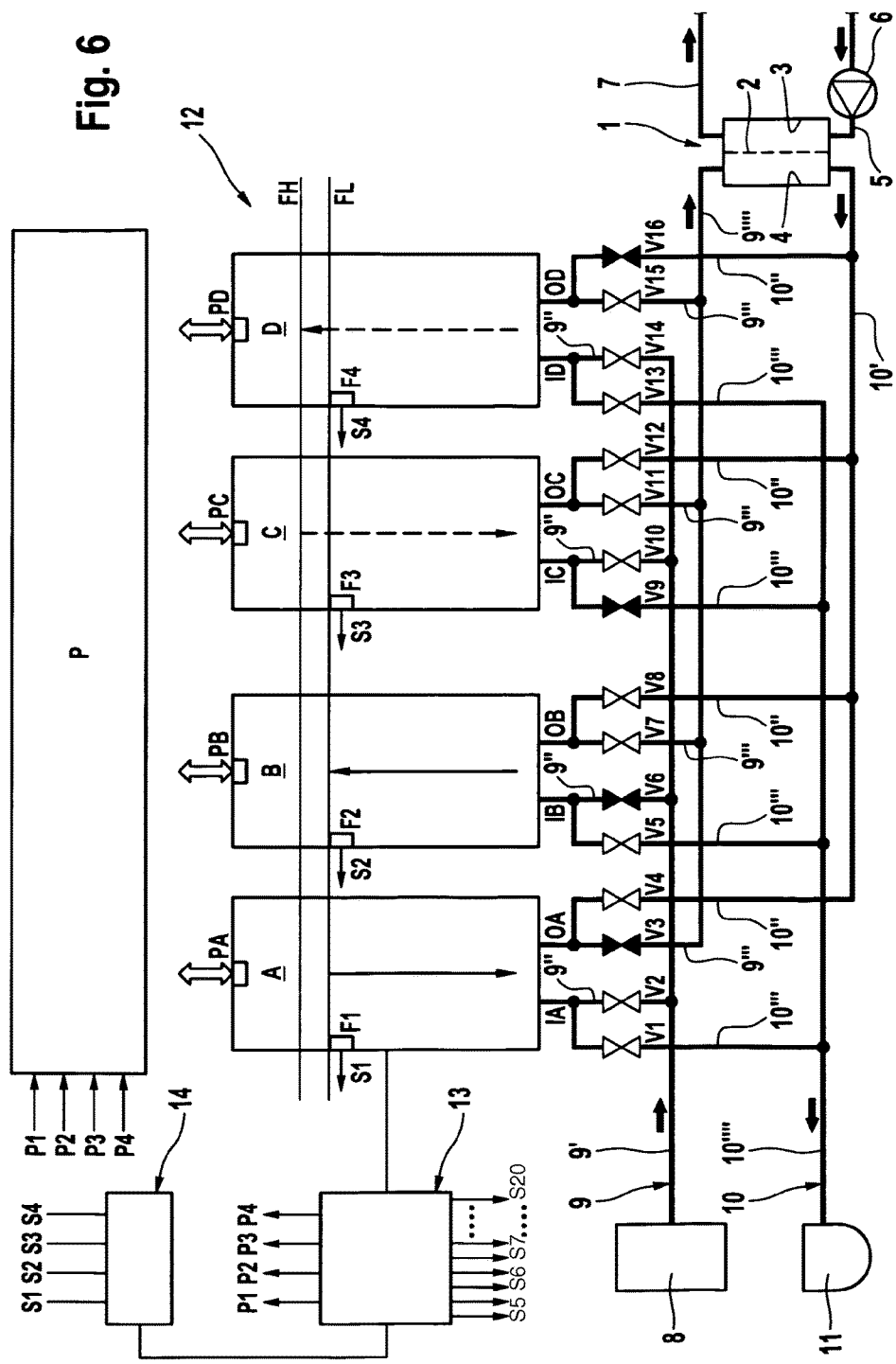

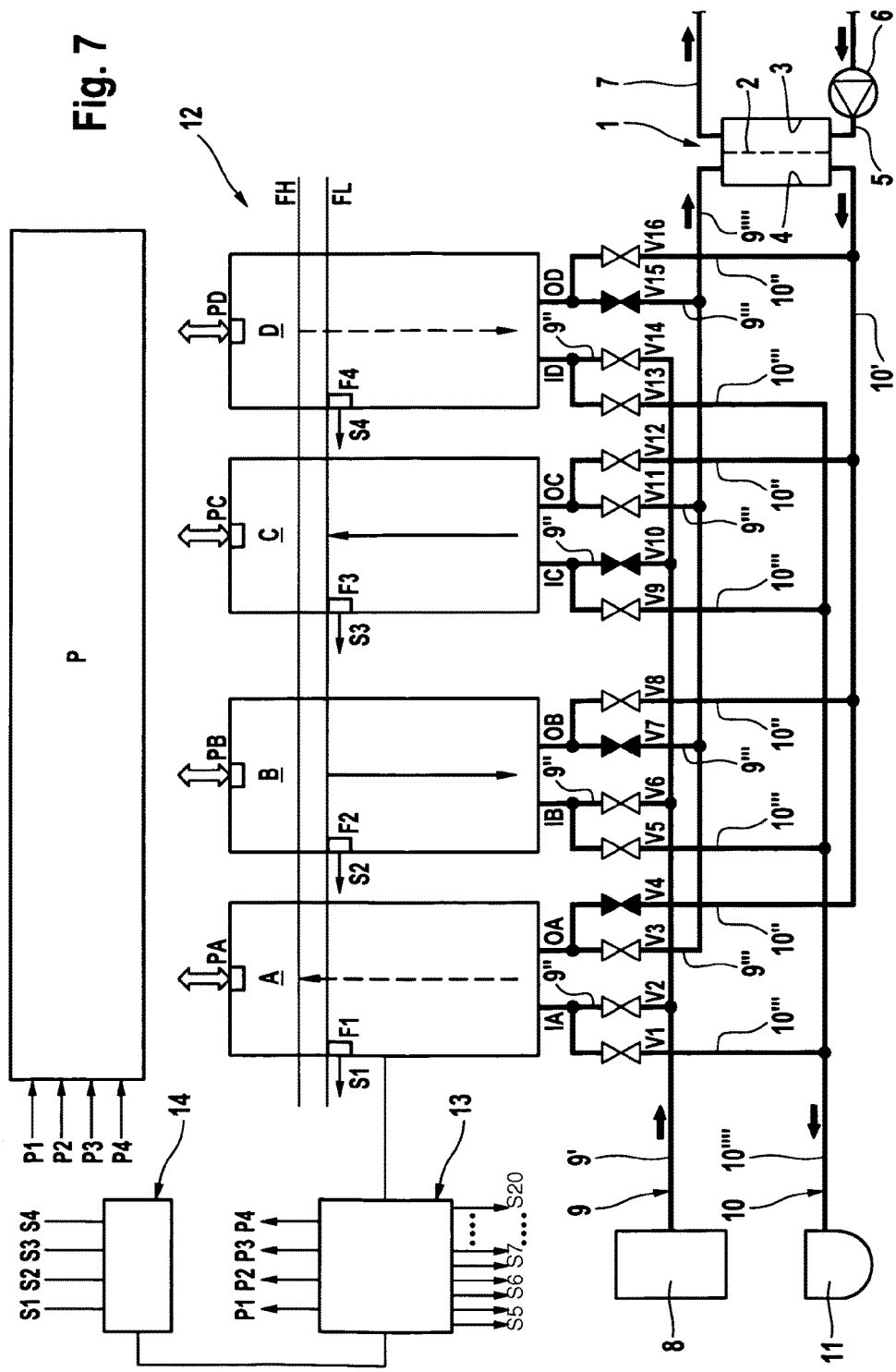

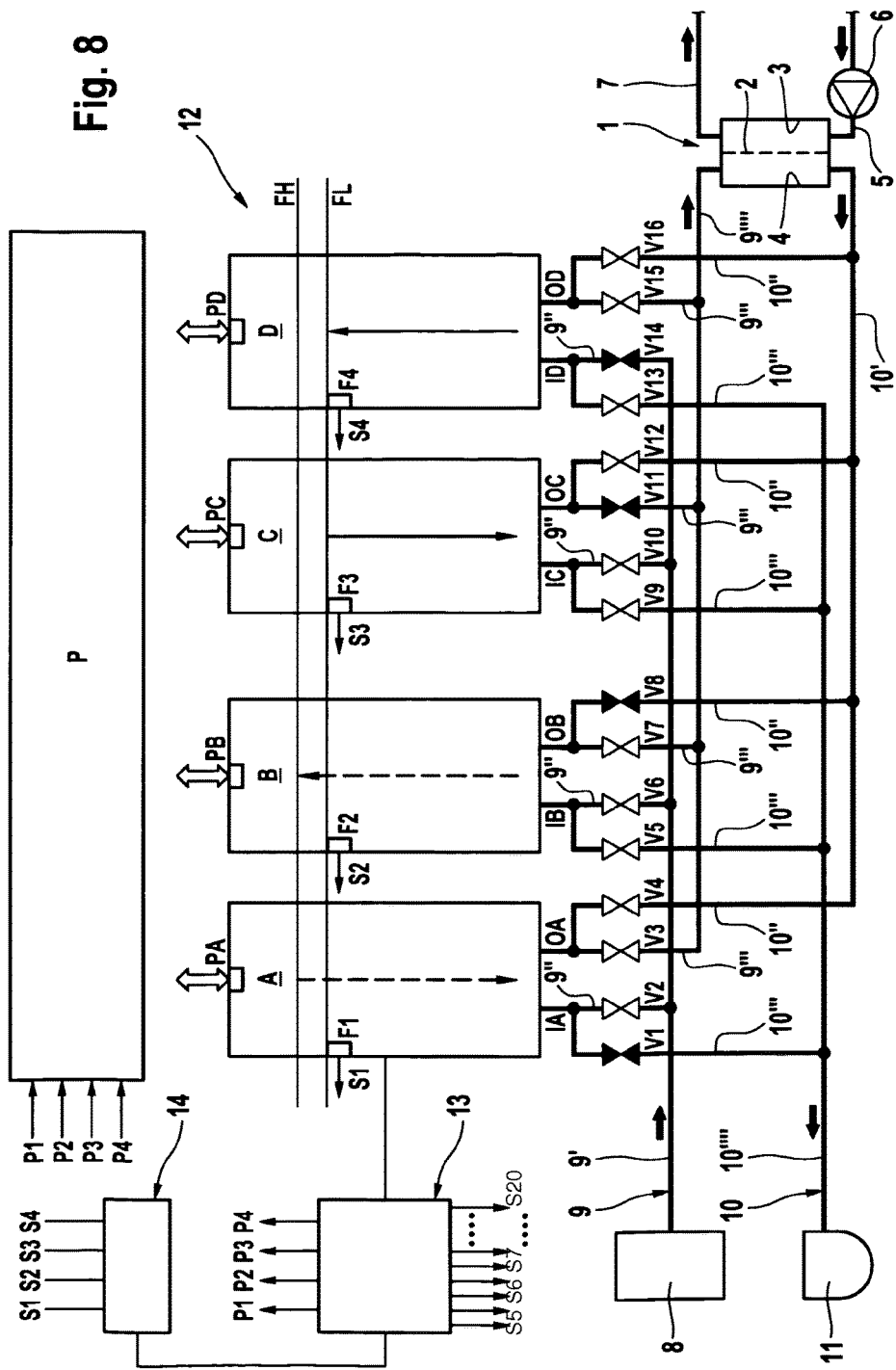

DEVICE AND METHOD FOR DETECTING BLOOD OR BLOOD CONSTITUENTS IN THE LIQUID SYSTEM OF A DEVICE FOR EXTRACORPOREAL BLOOD TREATMENT

CROSS REFERENCE TO RELATED APPLICATIONS

This is a 371 national phase application of PCT/EP2010/005826 filed Sep. 23, 2010, which claims priority from German Patent Application No. 10 2009 043 284.1 filed Sep. 29, 2009 and German Patent Application No. 10 2009 048 561.9 filed Oct. 7, 2009, all of which are incorporated herein by reference.

FIELD OF INVENTION

The present invention relates to an apparatus for dialysis treatment which has means for balancing fresh and used dialysis fluid. As well as this, the present invention also relates to a method of balancing fresh and used dialysis fluid.

BACKGROUND OF THE INVENTION

In cases of chronic kidney failure, various methods of cleansing or treating blood by means of apparatus are used to remove substances needing to be excreted and to withdraw fluid. In hemodialysis (HD), the predominant mechanism is the diffusive movement of substances, whereas in hemofiltration (HF) a convective movement of substances takes place through the semi-permeable membrane of the dialyzer or filter. Hemodiafiltration (HDF) is a combination of these two methods. When mention is made of a dialyzer in what follows, what a dialyzer is also understood to mean is a filter.

Because of the large amounts of material exchanged, there is in the above-mentioned methods a need for the fresh dialysis fluid fed to the dialyzer and the used dialysis fluid taken away from the dialyzer to be exactly balanced, with due allowance made for the quantity of fluid which is withdrawn from the patient through the membrane of the dialyzer, over the treatment time as a whole. The prior art includes gravimetric and volumetric balancing systems. In controlled dehydration, some or all of the amount of fluid which is withdrawn from the patient by ultrafiltration can be fed back to the patient in the form of pyrogen-free dialysate or substituate. The infeed of pyrogen-free dialysate or substituate to the extra-corporeal blood circuit at a point upstream of the dialyzer is referred to as predilution and the infeed of dialysate or substituate at a point downstream of the dialyzer is referred to as postdilution. The two methods may also be combined with one another.

DE A 28 38 414 describes a dialysis apparatus having a balancing system which has two balancing chambers, halves of which are filled alternately with fresh dialysis fluid while used dialysis fluid is expelled from whichever are the other halves of the chambers at the time. The part of the fluid circuit which is included between the balancing system and the dialyzer therefore acts as a closed system whose volume is constant. Fluid can be withdrawn from the closed system by means of an ultrafiltration pump. If fluid is withdrawn, a pressure gradient is set up at the semi-permeable membrane of the dialyzer and this gradient results in the same amount of fluid being withdrawn from the patient as is withdrawn from the closed system by the ultrafiltration pump.

For dialysis treatment, it is very important for the amount of fluid withdrawn from the patient by ultrafiltration to be able to be determined exactly. Very stringent requirements are therefore set for the accuracy of the balancing process. However, this presupposes that it is possible to achieve an exact balance of fresh and used dialysis fluid with the balancing chambers of the balancing system. Even slight errors in the balancing in the successive phases of operation of the balancing system may build up over the time taken by the treatment as a whole to misbalances which are no longer acceptable.

Volumetric balancing systems are known in which fresh and used dialysis fluid are fed respectively into and out of the balancing chambers by pumps. What are also known however are balancing systems in which balancing chambers divided into two halves by a membrane have a working fluid applied to them, to feed fresh or used dialysis fluid as the case may be.

DE A 198 30 928 describes a dialysis apparatus having a volumetric balancing system whose balancing chambers take the form of disposable items intended for once-only use. The balancing system comprises a total of four balancing chambers which are each divided into two halves by a membrane. For fresh or used dialysis fluid which is situated in one of the two halves of the chamber to be fed, a working fluid is applied to the other half of the chamber. The four balancing chambers form a first pair of balancing chambers which are intended to feed fresh dialysis fluid, and a second pair of balancing chambers which are intended to feed used dialysis fluid. The fresh dialysis fluid is fed by the two balancing chambers forming one pair of balancing chambers from a source of dialysis fluid to the dialysis-fluid chamber of the dialyzer. The used dialysis fluid from the dialysis-fluid chamber of the dialyzer is fed by the two balancing chambers forming the other pair of balancing chambers to a discharge. When this takes place, the halves of alternate balancing chambers are filled with fresh and used dialysis fluid in the respective cases, thus causing there to be a continuous flow of dialysis fluid through the dialysis-fluid chamber of the dialyzer.

To enable the respective balancing chambers to be filled alternately with fresh and used dialysis fluid, the relevant halves of the balancing chambers are connected, in the respective cases, into the infeed line for fresh dialysis fluid which runs from the source of dialysis fluid to the dialysis-fluid chamber of the dialyzer and into the takeaway line for used dialysis fluid which leads away from the dialysis-fluid chamber of the dialyzer and runs to the discharge. Situated in the respective segments of the infeed and takeaway lines are shut-off members to enable the flow of fluid to be controlled. The flow management and control system as a whole is neither intended nor suitable to allow the balancing chambers forming one pair of balancing chambers, which are intended to feed fresh dialysis fluid, to be used to feed used dialysis fluid and vice versa.

It is a disadvantage that, for exact balancing of fresh and used dialysis fluid, it is a prerequisite for the volumes of the individual halves of the balancing chambers to be exactly the same. This however makes great demands on the production tolerances, which can only be maintained with a great deal of technical cost and complication, particular in the case of an arrangement of balancing chambers which is designed to be a disposable item.

Also known, from US 2005/0000868 A1, is a balancing system which has four balancing chambers which are used to balance against one another the substituate or replacement fluid which is being fed to the patient and the filtrate or waste fluid which is withdrawn via the membrane of the dialyzer. In the case of this balancing system too, two chambers in each case form a pair of chambers which receive either substitute or filtrate. Pumps in the infeed and takeaway lines serve to fill and empty the chambers. For this reason the chambers themselves do not need to be divided into two halves by a membrane.

SUMMARY OF THE INVENTION

The object underlying the present invention is to provide an apparatus for dialysis treatment which allows exact balancing of fresh and used dialysis fluid. As well as this, it is also an object of the present invention to provide a method for the exact balancing of fresh and used dialysis fluid.

The apparatus according to the present invention for dialysis treatment and the method according to the present invention for balancing fresh and used dialysis fluid are characterized in that the individual balancing chambers of the balancing system receive both fresh dialysis fluid and also used dialysis fluid, the functions of the balancing chambers being alternately interchanged. In this way, exact balancing can be achieved even when the volumes of the individual chambers differ from one another. Over the period of the treatment as a whole, the differences between the volumes balance each other out due to the cyclic interchange of the chambers.

It is immaterial to the present invention how fresh and used dialysis fluid is fed to the individual balancing chambers and how fresh and used dialysis fluid is taken away from the individual balancing chambers.

In the apparatus according to the present invention for dialysis treatment, the means for conveying fresh and used dialysis fluid, which are preferably flexible lines, are so designed that fresh dialysis fluid can be fed from a source of dialysis fluid to each balancing chamber and fresh dialysis fluid can be fed from each balancing chamber to the dialysis-fluid chamber of a dialyzer, and used dialysis fluid can be fed from the dialysis-fluid chamber of the dialyzer to each balancing chamber and used dialysis fluid can be taken away from each balancing chamber. In successive phases of operation, the individual balancing chambers are each filled with fresh or used dialysis fluid, and the balancing chambers which have been filled with fresh or used dialysis fluid are emptied. The four balancing chambers form two pairs of balancing chambers with, in each phase of operation, fresh dialysis fluid being fed to the dialysis-fluid chamber from one balancing chamber of one pair of balancing chambers and used dialysis fluid being fed from the dialysis-fluid chamber to the other balancing chamber of the one pair of balancing chambers, while fresh dialysis fluid is fed from the source of dialysis fluid to one balancing chamber of the other pair of balancing chambers and used dialysis fluid is taken away from the other balancing chamber of the other pair of balancing chambers. In the successive phases of operation, the functions of the individual balancing chambers are interchanged with one another, thus enabling differences in the volumes of the balancing chambers to be compensated for over the period of treatment as a whole.

It is immaterial to the present invention how the dialysis fluid is fed to or from the balancing chambers. In a preferred embodiment of the present invention, a pressure above atmospheric or a pressure below atmospheric, by which the fresh and used dialysis fluid can be respectively forced into and sucked out of the chamber, is applied to the balancing chambers to allow fresh and used dialysis fluid to be fed. What is more, the means for feeding the dialysis fluid preferably have means for opening and shutting off the means for conveying dialysis fluid, and preferably means for opening and shutting off the flexible lines, to enable the flow of fluid to be controlled.

Basically, it is however also possible, as is known from the prior art, for a fluid rather than air to be used for the feeding of fresh and used dialysis fluid by the balancing chambers. However, it is then necessary for the two balancing chambers to be divided into two halves by a membrane, one half of the balancing chamber being used to receive fresh and used dialysis fluid and the other half of the balancing chamber being used to receive the working fluid. What is more, it is also possible for the dialysis fluid to be fed by pumps rather than by compressed air or a working fluid, as is known from the prior art.

Because two balancing chambers are connected together in each case, it is possible, basically, for a pressure above atmospheric to be generated in only one of the two balancing chambers while the other balancing chamber is vented. On the other hand however, it is also possible for a pressure below atmospheric to be generated in only one of the two balancing chambers while the other balancing chamber is vented. Preferably, a pressure above atmospheric is generated in one balancing chamber and a pressure below atmospheric is generated in the other balancing chamber.

In another preferred embodiment, the means for feeding dialysis fluid have means for measuring the level to which the balancing chambers are filled, the control unit being so designed that the means for opening and shutting off are opened and closed as a function of a preset value for the level to which the balancing chambers are filled. What is achieved in this way is that the flow of fluid is interrupted at a given filled level. This filled level need not be equal to the maximum volume of the balancing chambers which can be filled. For exact balancing of fresh and used dialysis fluid where the amount of fresh dialysis fluid is to exactly correspond to the amount of used dialysis fluid, the same value for the filled level is preset for all the balancing chambers.

An embodiment which is a particular preference makes provision for the possibility of fluid being fed to the patient or fluid being withdrawn from the patient throughout the period of the treatment. In this embodiment, two different values are preset for the level to which the balancing chambers filled. In this case one balancing chamber of one pair of balancing chambers, from which balancing chamber fresh dialysis fluid is fed to the dialysis-fluid chamber, is filled to the first value for the filled level, whereas the other balancing chamber of the one pair of balancing chambers, to which balancing chamber used dialysis fluid is fed from the dialysis-fluid chamber, is filled to a second value for the filled level, with the first value being different from the second value. Similarly, one balancing chamber of the other pair of balancing chambers, to which balancing chamber fresh dialysis fluid is fed from the source of dialysis fluid, is filled to the first value for the filled level, whereas the other balancing chamber of the other pair of balancing chambers, from which balancing chamber used dialysis fluid from the dialysis-fluid chamber is taken away, is filled to the second value for the filled level. The difference between the first and second values corresponds to the amount of fluid which is withdrawn from or fed to the patient through the membrane of the dialyzer. If the first value for the filled level is less than the second value for the filled level, filtrate is withdrawn from the patient's blood. Different values for the filled level may be preset in this case in one or more or in all of the phases of operation of a cycle, in which case only one, two, three or four chambers are differently filled. The amount withdrawn by ultrafiltration can be then be found from the sum of the differences between the levels to which the balancing chambers involved are filled. Because of the comparatively small differences between the filled levels, the deviations which the individual differences in volume show from the desired value for the ultrafiltration rate which has to be set by the treating physician, which deviations may possibly arise due to manufacturing tolerances or errors in measurement, are considerably smaller than the deviations which arise when the balancing chambers are operating in the normal way.

In a further preferred embodiment, the means for balancing fresh and used dialysis fluid take the form of disposable items intended for once-only use. It thus becomes unnecessary for the dialysis apparatus to be fitted with balancing chambers installed as fixed units. As well as this, the expensive sterilising of the fluid-carrying parts which would otherwise still be present in the machine is dispensed with. The forming of a balancing system as a disposable item is known per se to the person skilled in the art. A disposable item of this kind is known for example from DE 198 30 928 C1 and DE 195 46 028 C2.

BRIEF DESCRIPTION OF THE DRAWINGS

In what follows, two embodiments of the present invention will be explained in detail by reference to the drawings.

In the drawings:

FIG. 5 shows the dialysis apparatus of FIG. 1, the first phase of the cycle of operation being shown in the case of ultrafiltration, FIG. 6 shows the dialysis apparatus of FIG. 5, the second phase of operation being shown, FIG. 7 shows the dialysis apparatus, the third phase of operation being shown, FIG. 8 shows the dialysis apparatus, the fourth phase of operation being shown.

DETAILED DESCRIPTION OF THE DRAWINGS

Figure 1:
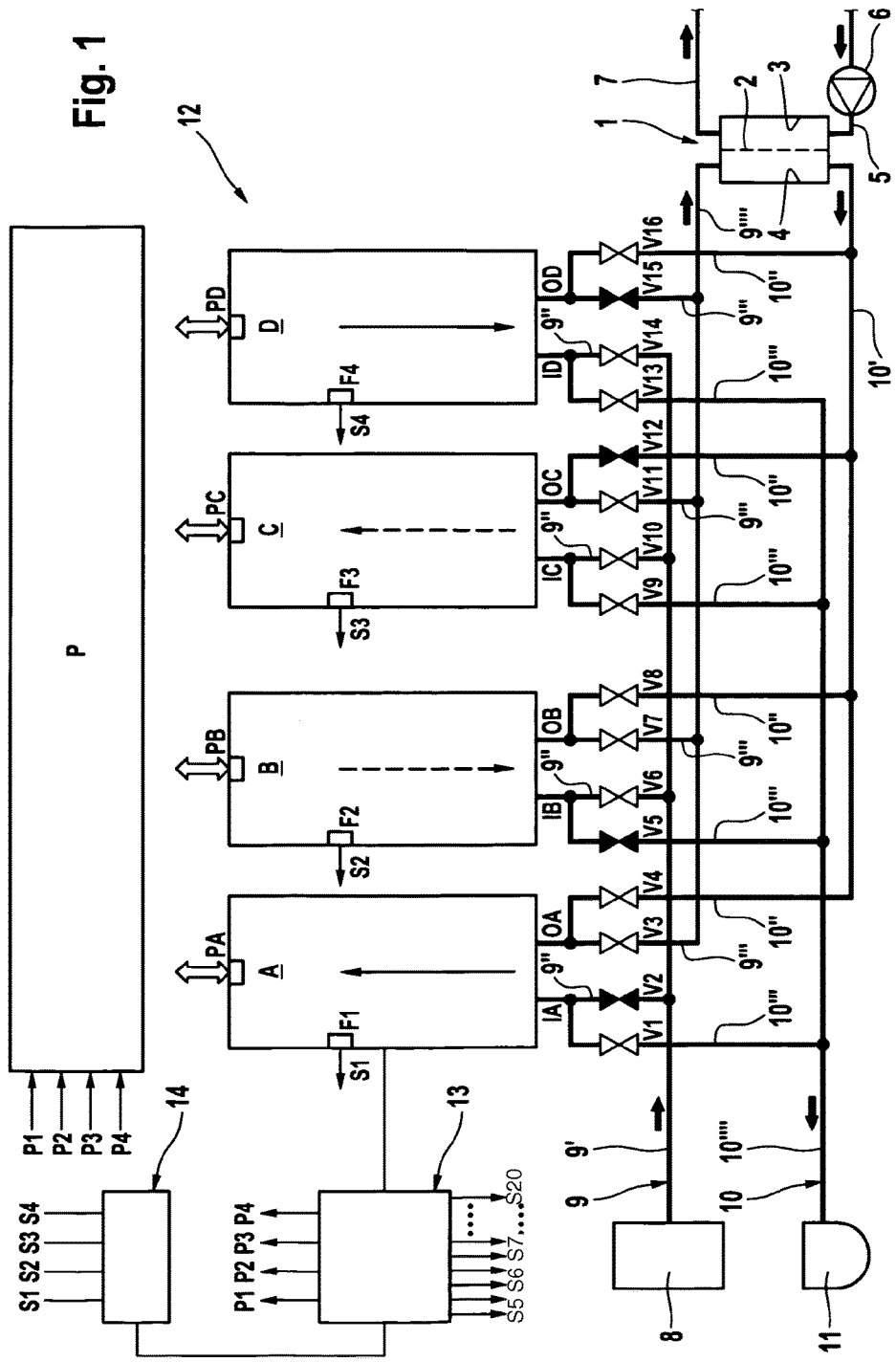
FIG. 1 is a highly simplified schematic view of an apparatus for dialysis, the first phase of operation of a cycle of operation being shown.
Figure 2:
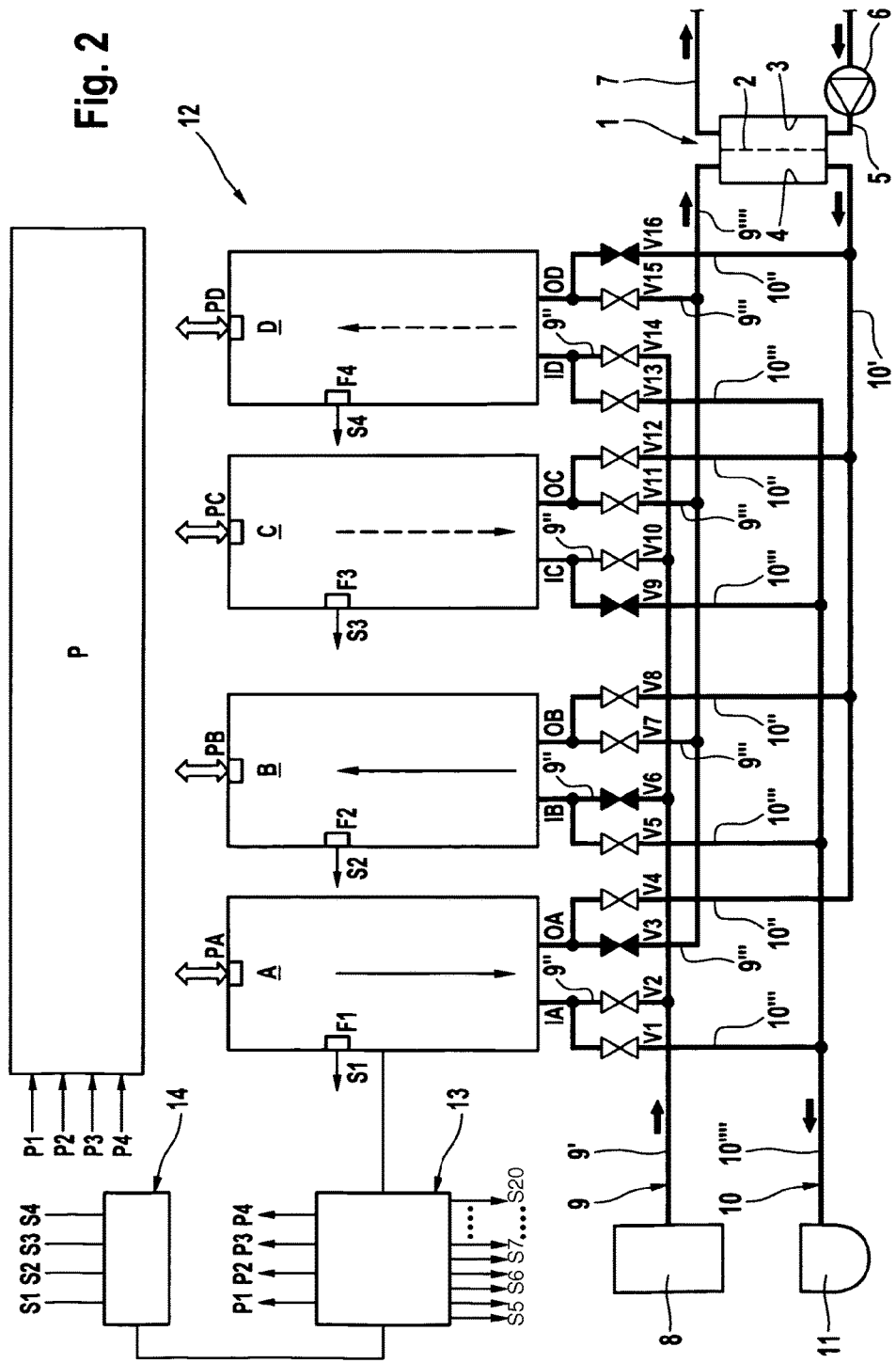
FIG. 2 shows the dialysis apparatus of FIG. 1, the second phase of operation of the cycle of operation being shown.
Figure 3:
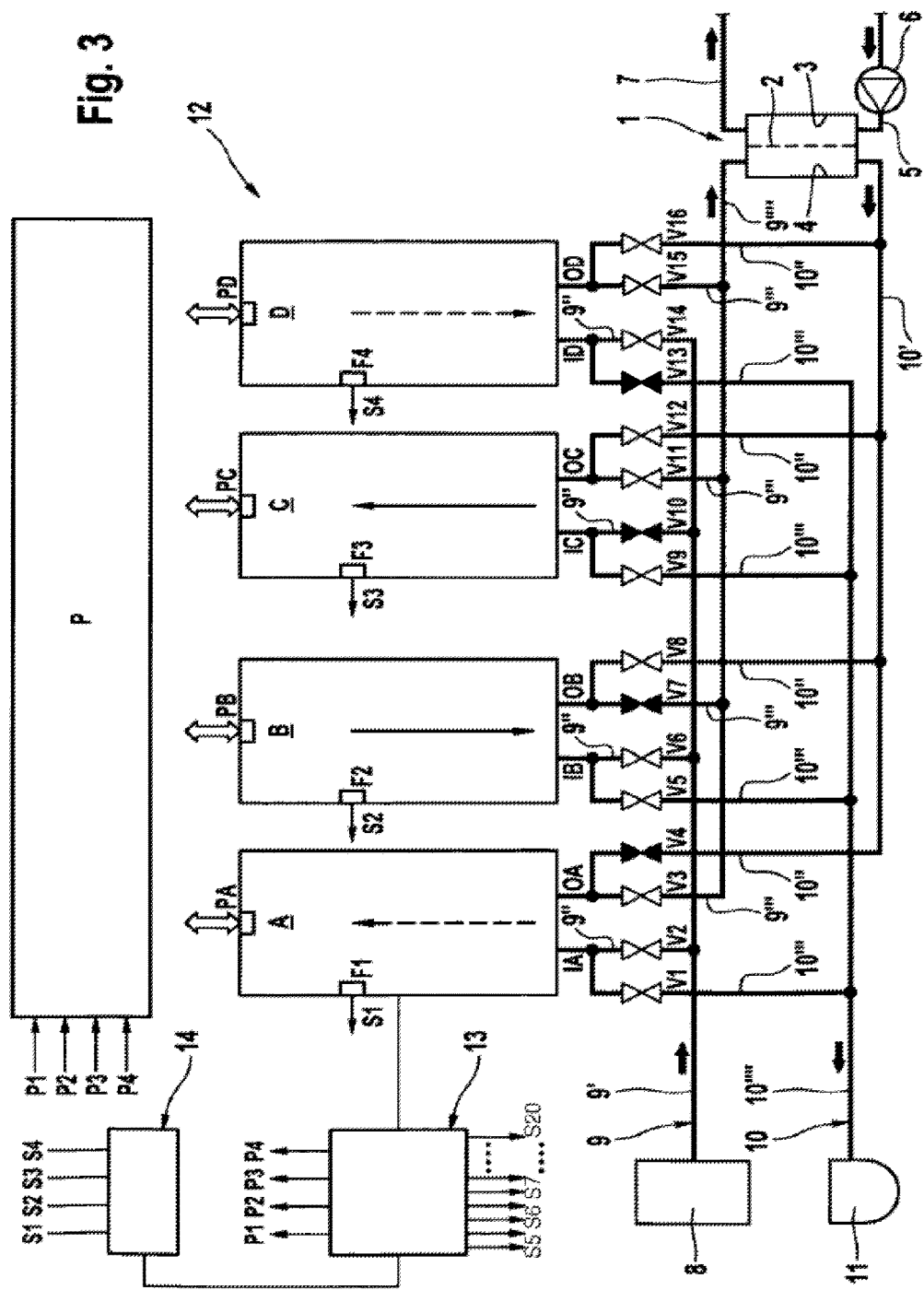
FIG. 3 shows the dialysis apparatus, the third phase of operation of the cycle of operation being shown.
Figure 4:
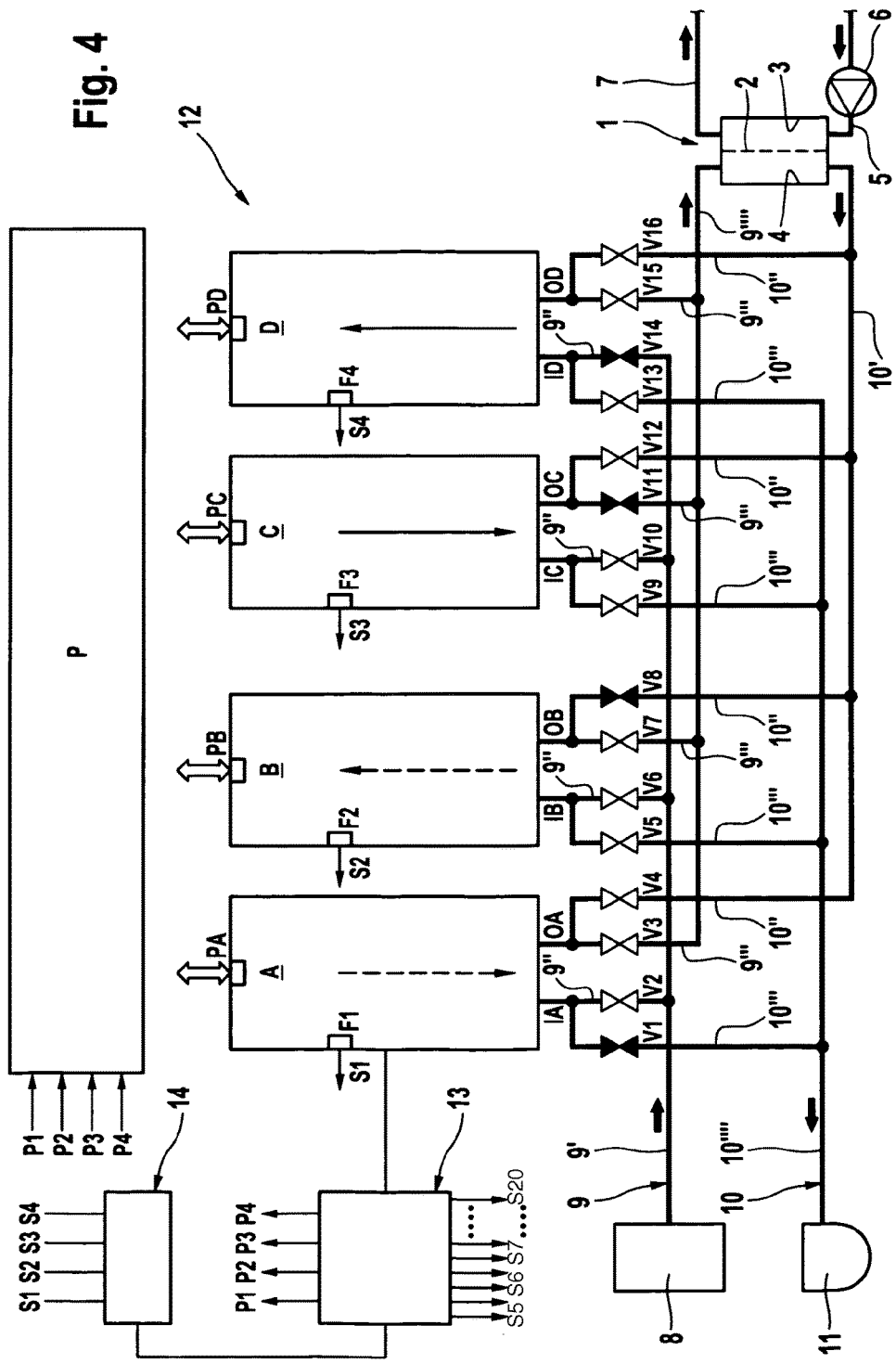
FIG. 4 shows the dialysis apparatus, the fourth phase of operation of the cycle of operation being shown.

FIGS. 1 to 4 are highly simplified schematic views of the main components of a dialysis apparatus, showing the individual phases of operation of a cycle of operation which comprises four phases of operation, in the case where no fluid is withdrawn from the patient. FIGS. 5 to 8 show the phases of operation of the dialysis apparatus in the case where fluid is withdrawn from the patient. The individual components of the dialysis apparatus are identified by the same reference numerals in the drawings.

The dialysis apparatus has a dialyzer 1 which is divided into a blood chamber 3 and a dialysis-fluid chamber 4 by a semi-permeable membrane 2. Connected to the inlet of the blood chamber 3 is a blood infeed line 5 into which a blood pump 6 is connected. Downstream of the blood chamber, a blood takeaway line 7 leads from the outlet of the blood chamber to the patient.

Fresh dialysis fluid is made available at a source 8 of dialysis fluid. From the source 8 of dialysis fluid, a dialysis-fluid infeed line 9 runs to the inlet of the dialysis-fluid chamber 4 of the dialyzer, while a dialysis-fluid takeaway line 10 runs from the outlet of the dialysis-fluid chamber of the dialyzer to a discharge 11. To allow fresh and used dialysis fluid to be balanced, a balancing arrangement is provided which will be explained in detail below.

The balancing arrangement 12 comprises a total of four balancing chambers which are identified as A, B, C and D. All the balancing chambers A, B, C, D are of the same construction. They are parts of a disposable item intended for once-only use. The balancing chambers A, B, C, D have respective inlets or outlets (connections) IA, IB, IC, ID and outlets or inlets (connections) OA, OB, OC, OD. As well as this the balancing chambers A, B, C, D also have respective connections PA, PB, PC, PD to which means P, of which only an indication is given, for generating a pressure above and/or below atmospheric in the balancing chambers A, B, C, D are connected.

The balancing chambers A, B, C, D are connected both into the dialysis-fluid infeed line 9 and into the dialysis-fluid takeaway line 10, the individual balancing chambers being able to be incorporated in the flow path for fluid or to be isolated from the flow path for fluid by associated shut-off members. The balancing chambers A, B, C, D each have four shut-off members associated with them, V1 to V16. The way in which the balancing chambers are connected will be described in detail below.

The dialysis-fluid infeed line 9 has a first portion 9' which leads away from the source 8 of dialysis fluid. Branching off from this first portion 9' of the line are four tapped-off lines 9" which run to respective ones of the inlets I of the four balancing chambers A, B, C, D.

Connected into the tapped-off lines 9" are the shut-off members V2, V6, V10 and V14. Running from the outlets of the balancing chambers A, B, C, D are respective tapped-off lines 9''' which run to a second portion 9'''' of the dialysis-fluid infeed line 9. The shut-off members V3, V7, V11 and V15 are connected into the tapped-off lines 9'''.

The dialysis-fluid takeaway line 10 has a first portion 10' which leads away from the outlet of the dialysis-fluid chamber 4 of the dialyzer 1. Branching off from this first portion 10' of the line are once again four tapped-off lines 10" which run to respective ones of the outlets O of the balancing chambers A, B, C, D. Connected into the tapped-off lines 10" are the shut-off members V4, V8, V12 and V16. Running from the inlets I of the balancing chambers A, B, C, D are respective tapped-off lines 10''' which run to a second portion 10'''' of the dialysis-fluid takeaway line 10. The shut-off members V1, V5, V9 and V13 are connected into the tapped-off lines 10''''.

As well as this, the dialysis apparatus also has a central control unit 13 which opens and closes the shut-off members V1-V16 by means of control lines S5-S20 and which, by means of control lines P1-P4, operates the means P for generating a pressure above or below atmospheric in such a way that a pressure above or below atmospheric is generated in the balancing chambers. The operation of the shut-off members may be performed electrically or pneumatically or hydraulically.

When the dialysis apparatus is operating, fresh dialysis fluid, which is made available at the source 8 of dialysis fluid, is balanced against used dialysis fluid, which is taken away to the discharge 11. The individual balancing chambers A, B, C, D are so operated in this case that they are filled with or emptied of fresh or used dialysis fluid as the case may be.

Operation takes place in successive cycles of operation which each comprise four phases of operation.

FIGS. 1 to 4 show the four phases of operation of one cycle of operation. The shut-off members which are opened by the control unit 13 are shown in black in this case. An upward pointing arrow indicates the filling of a balancing chamber, whereas a downward pointing arrow indicates the emptying of the balancing chamber. A solid arrow indicates fresh dialysis fluid whereas a dashed arrow indicates used dialysis fluid.

In the first phase of operation of the cycle of operation, the central control unit 13 opens the shut-off members V2, V5, V12 and V15 while it closes the other shut-off members (FIG. 1). The four balancing chambers can be divided in this way into a first pair of balancing chambers A, B and a second pair of balancing chambers C, D. Fresh dialysis fluid is fed to the balancing chamber A from the source 8 of dialysis fluid while used dialysis fluid is taken away from the balancing chamber B to the discharge 11. Fresh dialysis fluid is fed to the dialysis-fluid chamber 4 of the dialyzer 1 from the balancing chamber D, while used dialysis fluid is taken away from the dialysis-fluid chamber 4 of the dialyzer 1 to the balancing chamber C. The corresponding flows of fluid are indicated by arrows in FIG. 1. The content of the balancing chamber D is thus emptied into the balancing chamber C via the dialysis-fluid chamber of the dialyzer.

When this is done, a pressure below atmospheric is applied to the balancing chambers A and C to which fluid is fed, and a pressure below atmospheric is applied to the balancing chambers B and D from which fluid is taken away. For this purpose, the central control unit 13 operates the means P in the appropriate way to generate the pressures respectively above and below atmospheric.

The process of filling or emptying a chamber, as the case may be, is monitored by the central control unit 13. For this, the central control unit 13 co-operates with means 14 for monitoring the levels to which the individual balancing chambers A, B, C, D are filled, which means 14 have respective sensors F1, F2, F3, F4 for the filled level which are associated with the individual balancing chambers by means of respective control lines S1, S2, S3, S4. At a preset value for the filled level, which value is the same in all the chambers, the appropriate shut-off members V are closed.

In the second phase of operation, the chambers B and C form the first pair of balancing chambers while the chambers A and D form the second pair of balancing chambers. Fresh dialysis fluid is fed to the balancing chamber B from the source 8 of dialysis fluid while used dialysis fluid is taken away from the balancing chamber C to the discharge 11. Fresh dialysis fluid is fed to the dialysis-fluid chamber 4 from the balancing chamber A while used dialysis fluid from the dialysis-fluid chamber is fed to the balancing chamber D. When this is done, the appropriate shut-off members V are once again opened and a pressure above or below atmospheric is once again applied in the appropriate way to the balancing chambers by the means P for generating pressures respectively above and below atmospheric.

In the third phase of operation, the balancing chambers C and D form the first pair of balancing chambers and the balancing chambers A and B form the second pair of balancing chambers. Fresh dialysis fluid flows into the balancing chamber C from the source 8 of dialysis fluid while used dialysis fluid flows out of the balancing chamber D to the discharge 11. The fresh dialysis fluid from the balancing chamber B is emptied into the balancing chamber A via the dialysis-fluid chamber 4.

In the fourth phase of operation, the balancing chambers A and D form the first pair of balancing chambers while the balancing chambers B and C form the second pair of balancing chambers. Fresh dialysis fluid flows into the balancing chamber D while used dialysis fluid flows out of the balancing chamber A. At the same time, fresh dialysis fluid from the balancing chamber C is emptied into the balancing chamber B via the dialysis-fluid chamber 4.

After the fourth phase of operation, the first phase of operation of the next cycle of operation once again follows on. It can be seen that the functions of the individual balancing chambers are each time interchanged, in a cycle, with fresh dialysis fluid being fed to each balancing chamber and used dialysis fluid being taken away from each balancing chamber.

The cyclic interchange of the functions of the individual chambers A, B, C, D causes the different volumes of filling which are attributable to the different volumes of the chambers or to errors in the measurement of the filled levels to be compensated for during a cycle of operation. This will be explained in what follows by reference to the present embodiment.

Let it be assumed that the volume of fluid which can be filled into the balancing chamber A is 100 ml, that for the balancing chamber B is 110 ml, that for the balancing chamber C is 90 ml, and that for the balancing chamber D is 105 ml. The volume of fluid in the flexible lines will be ignored for the purposes of the example. However, it should be pointed out that the differences between the volumes of the chambers B, C, D and the desired value of 100 ml are unrealistically large and are only intended to serve as an example.

In the first phase of operation, the balancing chamber D is emptied into the balancing chamber C via the dialysis-fluid chamber 4 of the dialyzer 1. The means P for generating a pressure above or below atmospheric, which will be referred to below as the pneumatic means P, generate a pressure above atmospheric in chamber D and a pressure below atmospheric in chamber C. Therefore, 105 ml empties out of chamber D, but the shut-off member V12 in the inlet tract to chamber C closes after only 90 ml. Because chamber D has not been completely emptied, the shut-off member V15 in the outlet tract from this chamber remains open and the pressure above atmospheric from chamber D spreads into the dialysis-fluid chamber 4. There, the remaining fluid is forced through the semi-permeable membrane 2 from the dialysis-fluid side to the blood side due to the pressure gradient. Hence, 15 ml of fluid is fed into the patient's blood (refiltration).

In the second phase of operation, the chamber A empties into chamber D via the dialysis-fluid chamber 3. Because the volume of chamber D is greater than that of chamber A but its filled level is the same, the pressure below atmospheric is maintained in chamber D. Because of this, 15 ml of fluid is sucked from the blood side to the dialysate side through the membrane 2 of the dialyzer (filtration).

In the third phase of operation, chamber B empties into chamber A. The refiltration of 10 ml of dialysis fluid occurs. In the fourth phase of operation chamber C empties into chamber B. The filtration of 20 ml of dialysis fluid occurs.

If a balance sheet is now drawn up for the change in volume in the patient's blood, it becomes clear that the differences in the volumes of the chambers are compensated for over a cycle of operation. What is found is a sum of 15 ml−5 ml+10 ml−20 ml=0. Hence fluid is neither fed to nor withdrawn from the patient.

It will be shown below how a balancing error occurs if the chambers are not interchanged in a cycle, i.e. if the cycle of operation comprises only two phases of operation, with one pair of chambers receiving only fresh dialysis fluid and the other pair receiving only used dialysis fluid in each phase. In the first phase of operation, the chamber D would empty into the chamber C. There would be 15 ml of refiltration. In the second phase of operation, the chamber A would empty into the chamber B. There would be 10 ml of filtration. What this would give within the cycle of operation would be a sum which was 15 ml−10 ml+15 ml−10 ml=10 ml. Hence the error is not compensated for.

As well as allowing exact balancing of fresh and used dialysis fluid, the operation in accordance with the present invention of the balancing chambers also has the advantage that, for a case where ultrafiltration is wanted within a cycle of operation, the amount of ultrafiltration can be exactly set.

For the case where there is ultrafiltration, the central control unit 13 presets two different values for the levels FH and FL to which the chambers are filled, as will be explained below.

To allow fluid to be withdrawn from the patient's blood (ultrafiltration), the levels to which those balancing chambers which are to receive used dialysis fluid from the dialysis-fluid chamber are filled are set in such a way that their filled level FH is above the level FL to which those balancing chambers which are filled with fresh dialysis fluid are filled. The difference between the two filled levels FH−FL then corresponds to the fluid which is withdrawn from the patient's blood. FIGS. 5 to 8 show the phases of operation in the cycle of operation in the case of ultrafiltration. FIGS. 5 to 8 correspond to FIGS. 1 to 4. However, in FIGS. 5 to 8 the different levels FH, FL to which the chambers A, B, C, D are filled are indicated by lines. Except for the different levels to which the individual balancing chambers are filled, the operation of the balancing chambers takes place in the same way as was described by reference to FIGS. 1 to 4.

In the embodiment shown in FIGS. 5 to 8, all the balancing chambers for receiving used dialysis fluid are operated with a higher filled level than the balancing chambers which supply fresh dialysis fluid. However, it is also possible for only one, two, or three of the total of four balancing chambers for receiving the used dialysis fluid to be operated with a higher filled level.

In the first phase of operation, the fresh dialysis fluid is transferred from the balancing chamber D, which had been filled to the filled level FL in a previous phase of operation, to the balancing chamber C via the dialysis-fluid chamber 4 of the dialyzer 1, the balancing chamber C being filled to a filled level FH which is higher than the filled level FL. This is made clear by the lines in FIG. 5. Because the system is a closed one of constant volume, that amount of fluid which corresponds to the difference $\Delta=FH-FL$ between the two filled levels is withdrawn from the patient's blood through the membrane 2 of the dialyzer 1. In the second phase of operation, the dialysis fluid from the balancing chamber A is transferred to the balancing chamber D via the dialysis-fluid chamber, that amount of fluid which corresponds to the difference $\Delta=FH-FL$ between the two filled levels once again being withdrawn from the patient's blood.

The third and fourth phases of operation (FIGS. 7 and 8) correspond to the first and second phases of operation, with the same filled levels for the chambers. In this case too, an amount of fluid which corresponds to the difference $\Delta=FH-FL$ between the filled levels is withdrawn from the patient in each phase of operation. The amount of ultrafiltration is then found from the sum of all the differences in the filled levels in all the cycles of operation over the entire duration of the treatment. Because the differences between the filled levels are comparatively small, the desired amount of ultrafiltration can be set with relatively great accuracy.

What is claimed is:

1. An apparatus for dialysis treatment comprising:
a source of dialysis fluid for fresh dialysis fluid;
a dialyzer that is divided by a semi-permeable membrane into a blood chamber and a dialysis-fluid chamber;
a balancing system for balancing fresh and used dialysis fluid, which comprises a first balancing chamber, a second balancing chamber, a third balancing chamber, and a fourth balancing chamber;
a conveying system for conveying fresh dialysis fluid into each of the four individual balancing chambers and for taking used dialysis fluid away from each of the four individual balancing chambers;
a feeding system for feeding fresh and used dialysis fluid;
a discharge for receiving used dialysis fluid; and
a control system configured to operate the feeding system, wherein the conveying system is configured such that fresh dialysis fluid can be fed from the source of dialysis fluid to each of the first, second, third, and fourth balancing chambers and fresh dialysis fluid can be fed from each of the first, second, third, and fourth balancing chambers to the dialysis-fluid chamber, and used dialysis fluid can be fed from the dialysis-fluid chamber to each of the four individual balancing chambers and used dialysis fluid can be taken away from each of the four individual balancing chambers, and
wherein the control system is configured to cooperate with the feeding system to perform a cycle of individual phases in such a way that,
in a first phase of a cycle of operation, fresh dialysis fluid is fed to the first balancing chamber from the source of dialysis fluid while used dialysis fluid is taken away from the second balancing chamber to the discharge, and fresh dialysis fluid is fed to the dialysis-fluid chamber from the fourth balancing chamber while used dialysis fluid is taken away from the dialysis-fluid chamber and fed to the third balancing chamber,
in a second phase of the cycle of operation, fresh dialysis fluid is fed to the second balancing chamber from the source of dialysis fluid while used dialysis fluid is taken away from the third balancing chamber to the discharge, and fresh dialysis fluid is fed to the dialysis-fluid chamber from the first balancing chamber while used dialysis fluid from the dialysis-fluid chamber is fed to the fourth balancing chamber,
in a third phase of the cycle of operation, fresh dialysis fluid flows into the third balancing chamber from the source of dialysis fluid while used dialysis fluid is taken away from the fourth balancing chamber to the discharge, and fresh dialysis fluid is fed to the dialysis-fluid chamber from the second balancing chamber while used dialysis fluid from the dialysis-fluid chamber is fed to the first balancing chamber, and
in a fourth phase of the cycle of operation, fresh dialysis fluid flows into the fourth balancing chamber from the source of dialysis fluid while used dialysis fluid is taken away from the first balancing chamber to the discharge, and fresh dialysis fluid is fed to the dialysis-fluid chamber from the third balancing chamber while used dialysis fluid from the dialysis-fluid chamber is fed to the second balancing chamber.

2. The apparatus according to claim 1, wherein the feeding system comprises:
   a pressurizing system for applying a pressure above or below atmospheric pressure to the individual balancing chambers, and
   a shut-off system for opening and shutting off the conveying system.

3. The apparatus according to claim 2, wherein the feeding system has a measurement system for measuring a volume to which the individual balancing chambers are filled with dialysis fluid, and wherein the control system is configured such that the shut-off system for opening and shutting off the conveying system is opened and closed as a function of a preset value for a volume to which the individual balancing chambers are to be filled with dialysis fluid.

4. The apparatus according to claim 3, wherein, for the first phase of the individual phases, the control system is configured such that:
   a first value is preset for a volume of fresh dialysis fluid that is to be fed to the dialysis-fluid chamber from the fourth balancing chamber, and
   a second value is preset for a volume of used dialysis fluid that is to be fed from the dialysis-fluid chamber into the third balancing chamber,
   the first value being different from the second value.

5. The apparatus according to claim 4, wherein, for the third phase of the individual phases, the control system is configured such that:
   a third value is preset for a volume of fresh dialysis fluid that is to be fed from the source of fresh dialysis fluid into the third balancing chamber, and a fourth value is preset for a volume of used dialysis fluid that is to be taken away from the fourth balancing chamber,
   the third value being different from the fourth value.

6. The apparatus according to claim 4, wherein the first value is less than the second value.

7. The apparatus according to claim 1, wherein the conveying system comprises:
   an infeed line for feeding fresh dialysis fluid from the source of dialysis fluid to an inlet of the dialysis-fluid chamber; and
   a takeaway line for taking used dialysis fluid away from the dialysis-fluid chamber of the dialyzer,
   wherein the first balancing chamber, the second balancing chamber, the third balancing chamber, and the fourth balancing chamber are each configured such that they are connected to both the infeed line and the takeaway line.

8. The apparatus according to claim 7, further comprising:
   tapped-off lines that run to the infeed line and tapped-off lines that run to the takeaway line, said tapped-off lines branching off from each of the first balancing chamber, the second balancing chamber, the third balancing chamber, and the fourth balancing chamber,
   wherein the shut-off system comprises shut-off members that are arranged in the tapped-off lines.

9. The apparatus according to claim 1, wherein the four balancing chambers and the conveying system are in the form of disposable items.

10. A method of balancing fresh and used dialysis fluid with a balancing arrangement that has four individual balancing chambers comprising a first balancing chamber, a second balancing chamber, a third balancing chamber, and a fourth balancing chamber, the method comprising:
    operating the four individual balancing chambers to perform a cycle of individual phases in such a way that, in a first phase of a cycle of operation, fresh dialysis fluid is fed to the first balancing chamber from a source of dialysis fluid for fresh dialysis fluid while used dialysis fluid is taken away from the second balancing chamber to a discharge for receiving used dialysis fluid, and fresh dialysis fluid is fed to a dialysis-fluid chamber of a dialyzer from the fourth balancing chamber while used dialysis fluid is taken away from the dialysis-fluid chamber and fed to the third balancing chamber, wherein the dialyzer is divided by a semi-permeable membrane into a blood chamber and the dialysis-fluid chamber, in a second phase of the cycle of operation, fresh dialysis fluid is fed to the second balancing chamber from the source of dialysis fluid while used dialysis fluid is taken away from the third balancing chamber to the discharge, and fresh dialysis fluid is fed to the dialysis-fluid chamber from the first balancing chamber while used dialysis fluid from the dialysis-fluid chamber is fed to the fourth balancing chamber, in a third phase of the cycle of operation, fresh dialysis fluid flows into the third balancing chamber from the source of dialysis fluid while used dialysis fluid is taken away from the fourth balancing chamber to the discharge, and fresh dialysis fluid is fed to the dialysis-fluid chamber from the second balancing chamber while used dialysis fluid from the dialysis-fluid chamber is fed to the first balancing chamber, and in a fourth phase of the cycle of operation, fresh dialysis fluid flows into the fourth balancing chamber from the source of dialysis fluid while used dialysis fluid is taken away from the first balancing chamber to the discharge, and fresh dialysis fluid is fed to the dialysis-fluid chamber from the third balancing chamber while used dialysis fluid from the dialysis-fluid chamber is fed to the second balancing chamber.

11. The method according to claim 10, further comprising:
    generating a pressure above atmospheric pressure in the individual balancing chambers to feed dialysis fluid out of the individual balancing chambers; and
    generating a pressure below atmospheric pressure in the individual balancing chambers to feed dialysis fluid into the individual balancing chambers.

12. The method according to claim 10, further comprising, during the first phase of the individual phases:
    monitoring a volume of fresh dialysis fluid contained within the first balancing chamber as the first balancing chamber is being filled with the fresh dialysis fluid; and
    opening or closing a path for fluid into or out of the first balancing chamber as a function of a preset value of a volume of fresh dialysis fluid to which the first balancing chamber is to be filled.

13. The method according to claim 12, wherein:
    a first value is preset for a volume of fresh dialysis fluid that is to be fed to the dialysis-fluid chamber from the fourth balancing chamber during the first phase of the individual phases, and
    a second value is preset for a volume of used dialysis fluid that is to be fed from the dialysis-fluid chamber into the third balancing chamber during the first phase of the individual phases,
    the first value being different from the second value.

14. The method according to claim 13, wherein:
a third value is preset for a volume of fresh dialysis fluid that is be fed from the source of fresh dialysis fluid into the first balancing chamber during the first phase of the individual phases, and
a fourth value is preset for a volume of used dialysis fluid that is to be taken away from the second balancing chamber during the first phase of the individual phases,
the third value being different from the fourth value.

15. The method according to claim 13, wherein the first value is less than the second value.

16. The method according to claim 14, wherein the third value is less than the fourth value.

17. The method according to claim 10, further comprising:
monitoring volumes of dialysis fluid with which the individual balancing chambers are respectively filled; and
opening and/or closing paths for fluid into or out of each of the individual balancing chambers as a function of preset values of the volumes of dialysis fluid with which the individual balancing chambers are respectively to be filled.

* * * * *